US009428721B2

(12) United States Patent
Taniguchi et al.

(10) Patent No.: US 9,428,721 B2
(45) Date of Patent: Aug. 30, 2016

(54) CELL CULTURE OF FETAL LIVER IN LAYERED STATE IN A PARTITIONED MICRO-SPACE

(75) Inventors: Hideki Taniguchi, Yokohama (JP); Yun-Wen Zheng, Yokohama (JP); Go Tazaki, Tsukuba (JP); Tomoko Kosaka, Tsukuba (JP); Hitoshi Tsuruta, Ibaraki (JP); Motohiro Fukuda, Tsukuba (JP)

(73) Assignees: Public University Corporation Yokohama City University, Yokohama-shi (JP); KURARAY Co., Ltd., Kurashiki-shi (JP)

( * ) Notice: Subject to any disclaimer, the term of this patent is extended or adjusted under 35 U.S.C. 154(b) by 679 days.

(21) Appl. No.: 12/866,581

(22) PCT Filed: Feb. 5, 2009

(86) PCT No.: PCT/JP2009/051990
§ 371 (c)(1),
(2), (4) Date: Nov. 9, 2010

(87) PCT Pub. No.: WO2009/099152
PCT Pub. Date: Aug. 13, 2009

(65) Prior Publication Data
US 2011/0045500 A1    Feb. 24, 2011

(30) Foreign Application Priority Data
Feb. 6, 2008   (JP) ................................. 2008-026384

(51) Int. Cl.
| C12N 5/00 | (2006.01) |
| C12M 1/00 | (2006.01) |
| C12M 1/32 | (2006.01) |
| G01N 33/50 | (2006.01) |

(52) U.S. Cl.
CPC ............ *C12M 23/22* (2013.01); *C12M 23/12* (2013.01); *G01N 33/5073* (2013.01)

(58) Field of Classification Search
None
See application file for complete search history.

(56) References Cited

U.S. PATENT DOCUMENTS

2007/0166771 A1    7/2007   Kapur et al.

FOREIGN PATENT DOCUMENTS

| EP | 1 840 207 | 10/2007 |
| JP | 8 308562 | 11/1996 |
| JP | 8 319317 | 12/1996 |
| JP | 2002 525600 | 8/2002 |
| JP | 2006-191809 | 7/2006 |
| WO | 2007 105418 | 9/2007 |
| WO | 2007 149926 | 12/2007 |
| WO | 2008 130025 | 10/2008 |

OTHER PUBLICATIONS

Eschbach, E. et al., "Microstructured Scaffolds for Liver Tissue Cultures of High Cell Density: Morphological and Biochemical Characterization of Tissue Aggregates", Journal of Cellular Biochemistry, vol. 95, pp. 243-255 (2005).
Khetani, S. R. et al., "Microscale Culture of Human Liver Cells for Drug Development", Nature Biotechnology, vol. 26, No. 1, pp. 120-126 (Jan. 2008).
Kane, B. J. et al., "Liver-Specific Functional Studies in a Microfluidic Array of Primary Mammalian Hepatocytes", Analytical Chemistry, vol. 78, No. 13, pp. 4291-4298, (Jul. 1, 2006).
Azuma, H. et al., "Enrichment of Hepatic Progenitor Cells From Adult Mouse Liver", Hepatology, vol. 37, pp. 1385-1394 (Jun. 2003).
Karp, J. M. et al., "Controlling Size, Shape and Homogeneity of Embryoid Bodies Using Poly (Ethylene Glycol) Microwells+", Lab Chip, vol. 7, pp. 786-794 (2007).
U.S. Appl. No. 13/229,087, filed Sep. 9, 2011, Tazaki, et al.
Mohr et al, "3-D microwell culture of human embryonic stem cells", *Biomaterials*, vol. 27 (2006) pp. 6032-6042.
Lee et al, "Intrahepatic Stem Cell" The Korean Liver Cancer Study, issued 2002 (w/ partial English translation).
Symposia of The 123th annual meeting of the Pharmaceutical Society of Japan, 2003, p. 99, 28[P2]I-568 (with English translation of relevant part).
Massimo Sargiacomo, et al., "Long-term cultures of human fetal liver cells: a three-dimensional experimental model for monitoring liver tissue development", Journal of Hepatology, vol. 28, 1998, pp. 480-490.
Final Office Action issued Aug. 25, 2015, in Korean patent application No. 2013-7006738 (w/ English translation of relevant part).
Oertel et al, "Stem cells, cell transplantation and liver repopulation", *Biochimica et Biophysica Acta*, (2008) vol. 1782, pp. 61-74.

*Primary Examiner* — Blaine Lankford
(74) *Attorney, Agent, or Firm* — Oblon, McClelland, Maier & Neustadt, L.L.P

(57) ABSTRACT

Provided is a cell culture method whereby an in vivo function can be sustained over a long period of time and culture can be conducted using the minimum number of cells required. The cell culture method includes culturing undifferentiated cells in a layered state in a partitioned micro-space and obtains differentiated cells. When screening a pharmaceutical agent, undifferentiated cells capable of differentiating into liver cells, intestinal epithelial cells, nerve cells, myocardial cells and vascular endothelial cells are preferred. Particularly, in the prediction of pharmacokinetics or the like for humans, human cells are preferred.

15 Claims, 2 Drawing Sheets

CELL CULTURE OF FETAL LIVER IN LAYERED STATE IN A PARTITIONED MICRO-SPACE

TECHNICAL FIELD

The present invention relates to a cell culture method and a screening method.

BACKGROUND ART

A technique of using cells isolated from tissue for tests and examinations is essential in biotechnology-related fields. Such a technique is widely used for a diagnosis of diseases and pathoses, a search for a new drug and an assessment of its effect, an animal inspection, a plant inspection, a test of an environment pollutant and so on. Therefore, cells used in the biotechnology field are becoming increasingly diversified.

Although some isolated cells are immediately used for tests in a floating state, others are cultured in a state of being adherent to a culture dish and used for various tests and examinations in most cases. Primary cells and cell lines used for cell culture are required to exhibit drug sensitivity, toxicity reaction or the like of a similar level to a test in vivo, so-called an in vivo test. In other words, an in vivo-like cell function is required in a cell culture container. Further, because isolation for obtaining primary cells is complicated and cell culture lines used for a cell culture test are expensive, a test method with a small number of cells is desired.

Recently, discontinuation of development in the clinical testing phase has been an issue. This is due to an animal species difference in the pharmacokinetics study phase. Heretofore, in pharmacokinetics studies in the preclinical phase, in vivo pharmacokinetics has been predicted by using an animal such as a rat, a dog or a monkey. However, it has becoming evident that the prediction is virtually invalid in a clinical testing using a human. Therefore, in the prediction of pharmacokinetics or the like for humans, using a human sample is the most effective and convenient way, and it is important for conducting efficient drug development and safe clinical testing.

In the pharmacokinetics study that examines in vivo pharmacokinetics, absorption, metabolism and excretion in the liver are mainly examined, and a human sample to be used is liver slices, liver cells, liver microsomes or the like. Among those, the liver slices are not easily obtainable, and the liver microsomes can be used only for a metabolism test with limited metabolic enzymes. Thus, use of the liver cells is considered to be the most effective.

In screening, a culture dish to be used is a petri dish made of resin or a 6-well, 12-well, 48-well or 96-well plate. The size of the entire plate is substantially the same, and as the number of wells increases, the size of one well decreases. One well corresponds to one culture dish. Further, with the recent trend toward micronization, a 384-well plate made up of a larger number of culture dishes with a smaller diameter has been started to be used, and the one adaptable for a desired screening method is used. The bottom of such a culture dish is a flat-shaped, and the bottom surface is used as a culture surface.

However, if a hitherto-used culture dish is used for culture of tissue cells, there are cases where the original function disappears and dedifferentiation occurs and where undifferentiated cells do not differentiate, which raises an issue that a target cell function is not expressed. For example, if fresh human liver cells are cultured on a normal flat plate, the function of metabolic enzymes when isolated is significantly lowered in one day or so, and therefore a drug metabolism test is conducted in four hours from seeding the cells onto the plate in some cases. There is thus a problem that it is impossible to make use for a test with long-hours culture and a problem that it is impossible to investigate long-hours metabolic stability.

To overcome the above problems, an attempt to coat a culture container surface with a biological material (glycoprotein, protein etc.) of human or animal origin (cf. Patent Document 1), an attempt to culture in polymer gel (cf. Patent Document 2), and an attempt to form a liver cell mass in a micro-container (cf. Patent Document 3) have been made.

[Patent Document 1]
Japanese Unexamined Patent Application Publication No. 8-319317
[Patent Document 2]
Japanese Unexamined Patent Application Publication No. 8-308562
[Patent Document 3]
International Patent Publication No. WO2008/130025

DISCLOSURE OF INVENTION

Technical Problem

However, in the method disclosed in Patent Document 1, there are problems such that the biological material as coating is special and high cost, it is difficult to form a uniform cell assembly in a culture container, and the in vivo function cannot be sustained over a long period of time. In the method disclosed in Patent Document 2 also, there are problems such that the size of a cell assembly cannot be controlled, microscopic observation is not easy, and operability is complicated as a screening substrate. Further, because a commercially available dish or plate is used as a supporting container in both of the above methods, efficient screening with the minimum number of cells required is difficult. In the method disclosed in Patent Document 3 also, although improvement of liver cell metabolic activity in the early stage of culture is possible, maintaining the metabolic activity for two weeks or longer is difficult.

An object of the present invention is to provide a cell culture method whereby an in vivo function can be sustained over a long period of time and culture can be conducted using the minimum number of cells required.

Technical Solution

A cell culture method according to the present invention includes culturing undifferentiated cells in a layered state in a partitioned micro-space and obtaining differentiated cells. The layered state means that cells are laminated two or more layers. When screening a pharmaceutical agent, undifferentiated cells capable of differentiating into liver cells, intestinal epithelial cells, nerve cells, myocardial cells and vascular endothelial cells are preferred. Particularly, in the prediction of pharmacokinetics or the like for humans, undifferentiated cells are preferably human cells. The undifferentiated cells are preferably stem cells, precursor cells or the like.

Further, it is particularly preferred that the partitioned micro-space is a micro-container in a cell culture container having a plurality of micro-containers on a surface. The micro-container preferably has a bottom surface area of $9 \times 10^{-4}$ mm$^2$ to $9 \times 10^{-2}$ mm$^2$, and a side wall with a height of 15 μm to 300 μm and a width of 3 μm to 15 μm. Further, in order to facilitate microscopic observation, it is preferred that a region where the micro-container is formed in the cell culture container has transparency.

A screening method according to the present invention includes placing a plurality of cells cultured by the above-described culture method and screening a compound. Further, in order to conduct culture using the minimum number of cells required, it is preferred that the cell culture container includes a plurality of partitioned spots each made up of a plurality of micro-containers.

Advantageous Effects

According to the present invention, it is possible to provide a cell culture method whereby an in vivo function can be sustained uniformly over a long period of time and culture can be conducted using the minimum number of cells required.

EXPLANATION OF REFERENCE

10 Cell Culture Unit
11 MICRO-CONTAINER
12 SIDE WALL OF MICRO-CONTAINER
13 SPOT
14 SIDE WALL OF SPOT

BEST MODE FOR CARRYING OUT THE INVENTION

In the present invention, undifferentiated cells such as liver stem cells are cultured in a layered state with a uniform size in a micro-container, which is a partitioned micro-space. An especially important point in the invention is to use undifferentiated cells having proliferation potency, to culture in a partitioned micro-space, and to culture in a layered fashion. It is thereby possible to form a cell mass containing differentiated liver parenchymal cells, for example, and improve the function. Further, because liver stem cells undergo undifferentiated proliferation, it is possible to sustain the cell function. The present invention provides such a culture method and a screening method using the same.

On the surface of a culture container used in the culture method and the screening method according to the present invention, a pit and projection pattern or a plurality of micro-containers or a culture space is formed. By optimizing the width and the height of a side wall (projection) that partitions the micro-containers, it is possible to culture cells only in the micro-containers and maintain a uniform differentiated state. Note that a partitioned culture space made of gel may be formed instead of the micro-containers.

The dimensions of a micro-container surrounded by side walls should be in an optimum range for culturing cells. If the bottom surface area of the micro-container is too large, a cell partially extends thinly, and a uniform layered state is not formed as in the case of culture on a flat plate. On the other hand, if the bottom surface area of the micro-container is too small, a cell cannot be contained. Therefore, the dimensions of the space are preferably in the range to contain several to several tens of cells according to cell species to be cultured.

Further, the side wall of the micro-container also should be in an optimum range for culturing cells. If the width of the side wall is too wide, a cell adheres to the top surface of the side wall, which is unsuited to culture. If the width of the side wall is too narrow, preparation is difficult. If the height of the side wall is too low, a cell goes over the side wall, which is unsuited to culture. If the height of the side wall is too high, preparation is difficult and further the material is hard to diffuse, which degrades the culture environment.

Hereinafter, an embodiment of the present invention is described. Note that, however, the present invention is not limited to the following embodiment. Further, to clarify the explanation, the following description and the drawings are appropriately simplified.

Embodiment

Figure 1:
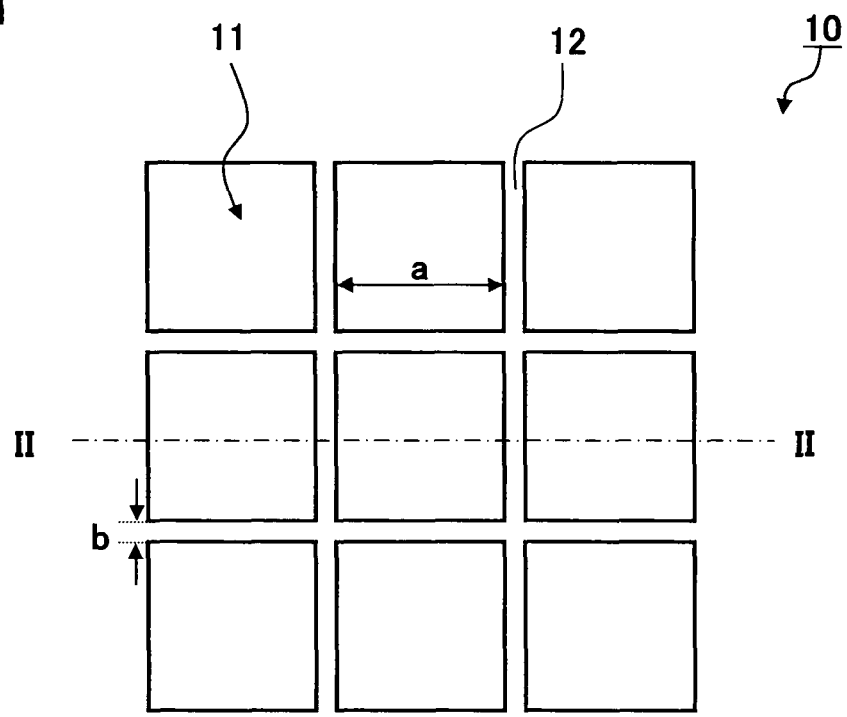
FIG. 1 is a plan view showing a structure of a cell culture container used for a cell culture method according to an example 1.
Figure 2:
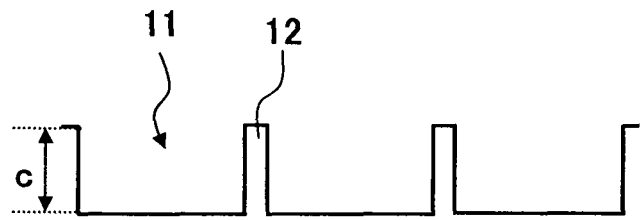
FIG. 2 is a cross-sectional view showing a structure of a cell culture container used for the cell culture method according to the example 1.

A structure of a micro-container of a cell culture unit used for cell culture according to an embodiment is described hereinafter with reference to FIGS. 1 and 2. FIG. 1 is a plan view showing a structure of a micro-container according to the embodiment, and FIG. 2 is a cross-sectional view along line II-II in FIG. 1. As shown in FIG. 1, a cell culture unit 10 includes a micro-container 11 and a side wall 12. On a culture surface of the cell culture unit 10, a plurality of side walls 12 are formed in a mesh pattern, and a space surrounded on all four sides by the side walls 12 is the micro-container 11.

In FIG. 1, the width a of the bottom surface of the micro-container 11, and the width b and the height c of the side wall 12 for partitioning the micro-containers 11 are shown. It is necessary to satisfy 3 μm≤b≤15 μm and c/b≥2. If the width b of the side wall 12 is more than 15 μm, a cell adheres to the top surface of the side wall, which is unsuited to culture. On the other hand, if the width b of the side wall 12 is less than 3 μm, preparation is difficult. If the height of the side wall is too low, a cell goes over the side wall, which is unsuited to culture. If the height c of the side wall 12 is less than two times the width b of the side wall 12, a cell cultured in the micro-container 11 goes over it and moves to the adjacent micro-container 11. Further, specifically, when human fetal liver cells are layered in a square micro-container with one side of 100 μm, the height c of the side wall 12 is preferably 15 μm to 300 μm, and more preferably 50 μm to 150 μm. If the height c of the side wall is too high, preparation is difficult and further the material is hard to diffuse, which degrades the culture environment. The side wall 12 may have a multi-step shape.

The bottom surface shape of the micro-container 11 is not particularly limited, and various shapes may be employed other than a square, circle, or polygonal shape. The bottom surface area is preferably $9 \times 10^{-4}$ mm$^2$ to $9 \times 10^{-2}$ mm$^2$. Further, an isotropic shape is preferable, and when the bottom surface has a rectangular shape, it is preferred that the long side is 1 to 1.5 times the short side.

Figure 3:
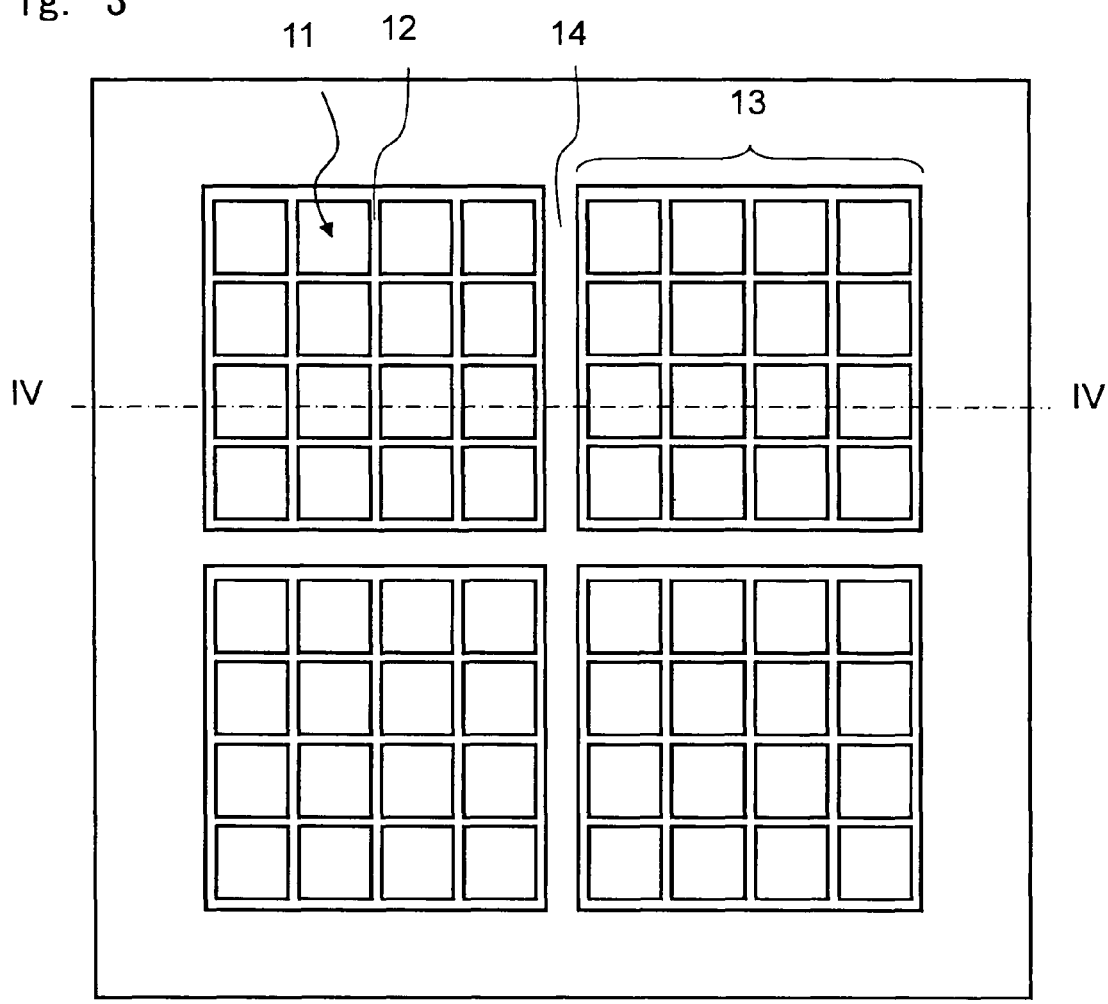
FIG. 3 is a plan view showing a structure of a cell culture container used for a screening method according to an embodiment.
Figure 4:
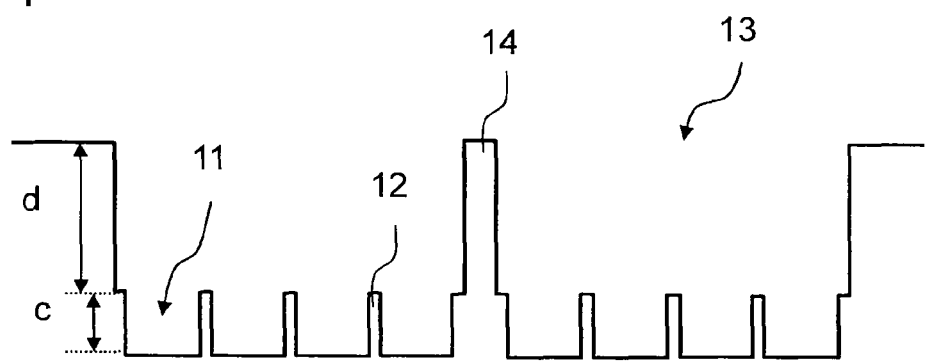
FIG. 4 is a cross-sectional view showing a structure of a cell culture container used for the screening method according to the embodiment.

The cell culture unit used in the present invention may have partitioned spots each made up of a plurality of micro-containers required for one screening as shown in FIGS. 3 and 4 in order to minimize the number of cells required. For example, in the case of using a micro-container in a square shape with one side of 200 μm and a height of 50 μm which provides a high differentiation efficiency when the minimum number of cells required for screening is about 1000, nine micro-containers are required; therefore, by preparing a spot in which the space is partitioned into nine micro-containers and providing a plurality of spots, it is possible to perform high-throughput screening that allows simultaneous examination of a plurality of reagents or pharmaceutical agents.

FIG. 3 is a plan view showing another structure of a cell culture unit according to the embodiment, and FIG. 4 is a cross-sectional view along line IV-IV in FIG. 3. FIG. 3 shows a side wall 14 that partitions a plurality of micro-containers and a partitioned spot 13. The height d of the side wall 14 may be set so that the capacity can keep a supernatant fluid such as a culture solution or a reaction solution without drying, and it can be defined appropriately.

Although a method of creating the pit and projection pattern of the cell culture unit according to the present invention is not particularly limited, it may be a method such as transcription molding using a mold, 3D optical modeling, precision machine cutting, wet etching, dry etching, laser processing or electrical discharge machining, for example. It is preferred to appropriately select such a manufacturing method in consideration of the purpose of the cell culture container, a required processing accuracy, a cost or the like.

As a specific example of the transcription molding method using a mold, a method of creating a pit and projection pattern by resin molding with use of a metal structure as a mold may be used. This method is preferable because it enables reproduction of the shape of the metal structure onto resin as a pit and projection pattern with a high transcription rate, and use of a general-purpose resin material can reduce a material cost. Such a method of using the metal structure is advantageous in that it is low cost and satisfies a high dimensional accuracy.

A method of manufacturing the above-described metal structure may be plating onto a resist pattern formed by photolithography or a resin pattern formed by 3D optical modeling, precision machine cutting, wet etching, dry etching, laser processing, electrical discharge machining or the like, for example. It is preferred to appropriately select the method in consideration of a purpose, a required processing accuracy, a cost or the like.

A method of forming a pit and projection pattern on resin by using the metal structure obtained above as a mold may be injection molding, press molding, monomer-cast molding, solvent cast molding, hot embossing molding, roll transcription by extrusion molding or the like, for example. It is preferred to use the injection molding in terms of productivity and mold transcription ability.

A material of a screening chip according to the present invention is not particularly limited as long as it has self-bearing properties, and synthetic resin, silicon, glass or the like may be used, for example. In terms of cost and cell visibility by microscopic observation, it is preferred to use transparent synthetic resin as a material.

The transparent synthetic resin may be acrylic resin such as polymethyl methacrylate and methyl methacrylate-styrene copolymer, styrene resin such as polystyrene, olefin resin such as cycloolefin, ester resin such as polyethylene terephthalate and polylactic acid, silicone resin such as polydimethylsiloxane, polycarbonate resin or the like, for example. Such resin may contain various kinds of additives such as coloring agent, dispersing agent and thickening agent within the range that does not lose transparency.

In the screening chip according to the present invention, surface treatment may be performed on the surface side of the pit and projection pattern to form a modified layer and/or a coating layer for the purpose of improving surface hydrophilicity, biocompatibility, cellular affinity or the like.

A method of forming the modified layer is not particularly limited as long as it is not a method that loses self-bearing properties or a method that causes extreme surface roughness of 100 μm or more, and it may be a method like chemical treatment such as drug treatment, solvent treatment and introduction of graft polymer by surface graft polymerization, or physical treatment such as corona discharge, ozone treatment and plasma treatment, for example.

Further, a method of forming the coating layer is not particularly limited, and it may be a method like dry coating such as sputtering and vapor deposition, wet coating such as inorganic material coating and polymer coating or the like, for example.

It is preferred to provide hydrophilicity onto the pit and projection pattern in order to inject a culture solution without mixing of air bubbles, and inorganic vapor deposition is preferable as a method to form a uniform hydrophilic film.

Further, in the case of taking cellular affinity into consideration, it is preferred to make coating of cytophilic protein such as collagen or fibronectin, for example. In order to uniformly coat a collagen solution or the like, it is preferred to make coating after forming the above-described hydrophilic film. Because culture on an extracellular matrix surface is generally desirable in cell culture in imitation of the in vivo environment, it is particularly preferred to provide an organic film made of extracellular matrix suitable for cultured cells after providing a uniform hydrophilic inorganic film as described above.

Cells to be cultured by the culture method and the screening method according to the present invention are preferably undifferentiated cells, and they may be liver stem cells, liver precursor cells, bowel stem cells, intestinal precursor cells, mesenchymal stem cells, cardiac muscle precursor cells, embryonic stem cells or the like, for example, and cell species may be appropriately selected according to the purpose of screening. For example, when the purpose is screening in assumption of metabolic response of a pharmaceutical agent in a liver, liver stem cells capable of differentiating into liver cells or the like are used. Particularly, human liver stem cells are used when the purpose is metabolic response of a pharmaceutical agent in a human.

The screening method according to the present invention places cells only in a micro-container for culturing cells and makes the function similar to that in vivo expressed in the space, and it is thus necessary to seed an appropriate number of cells. The cell seeding density is preferably $1.0 \times 10^4$-$5.0 \times 10^6$ cells/cm$^2$. For example, when the micro-container has a square shape with one side of 100 μm, it is preferably $1.0 \times 10^4$-$1.0 \times 10^5$ cells/cm$^2$.

When cells to be layered are liver cells or intestinal epithelium cells, it is preferred to measure the gene expression level, metabolic enzyme activity, transporter activity or the like and conduct screening.

Further, when cells to be layered are nerve cells or myocardial cells, it is preferred to measure the gene expression level, enzyme activity action potential or the like and conduct screening.

When cells to be layered are vascular endothelial cells, it is preferred to visually check vascularization and conduct screening.

EXAMPLE

Examples of the cell culture method according to the present invention are described hereinafter; however, the present invention is not limited to those examples.

<Culture Method of Fetal Liver Cells>

A frozen stock of human fetal liver cells was seeded onto type IV collagen coat dish (available from BD), cultured for about ten days, and proliferated. After that, on a pit and projection pattern substrate coated with 0.03% type IV collagen (available from Nitta Gelatin Inc.), liver cells were seeded at a rate of five cells in one micro-container ($3.8 \times 10^4$ cells/cm$^2$) and cultured for three weeks with 5% $CO_2$ and 37° C. The composition of a culture solution used was such that 10% fetal bovine serum, 1 μg/ml insulin, $1 \times 10^7$M dexamethasone, 10 mM nicotinamide, 2 mM L-glutamine, 50 μm β-mercaptoethanol, 5 mM HEPES, 59 μg/ml penicillin, 100 μg/ml streptomycin were added to a DMEM/F12 culture medium, and, from the first day after seeding, 25 ng/ml HGF, 20 ng/ml EGF, 10 ng/ml oncostatin M were further added to the culture solution. With use of a fresh culture medium of 0.5 mL having the same composition, a culture medium is replaced every several days.

<Gene Expression Analysis>

Gene expression of cytochrome P450 (CYP), which is a drug metabolizing enzyme of a liver, was evaluated by retrieving RNA from the cells that has been cultured for a predetermined number of days and conducting real-time PCR after cDNA synthesis.

Example 1

The pit and projection pattern shape shown in FIG. 1 where a=100 μm, b=10 μm and c=50 μm was created by photolithography, Ni electrolytic plating was performed, and a mold having the corresponding pit and projection shape was obtained. Using the mold, pattern transcription was made onto polystyrene by hot embossing molding, and a resin substrate with the above dimensions was produced. A silicon dioxide film of 100 nm was deposited on the resin substrate surface by vacuum deposition, γ-ray sterilization was performed, and thereby a pit and projection pattern substrate was obtained. After coating the pit and projection substrate with IV collagen, human fetal liver cells were cultured.

Comparative Example 1

Using a commercially available (Falcon(registered trademark) available from Becton, Dickinson and Company) γ-ray sterilized flat 24-well culture plate, after coating the plate with IV collagen, human fetal liver cells were cultured.

Table 1 shows the gene expression levels of CYP3A4, CYP2D6 and CYP2C9 after three weeks of culture in the example 1 and the comparative example 1. The table shows values when each CYP expression level after three weeks in the comparative example 1 is 1. In the example 1, the expression levels were higher than in the comparative example 1 for any CYP, and the function was sustained for three weeks of culture.

TABLE 1

|  | Example 1 | Comparative Example 1 |
|---|---|---|
| CYP3A4 | 4.5 | 1.0 |
| CYP2D6 | 8.5 | 1.0 |
| CYP2C9 | 2.3 | 1.0 |

INDUSTRIAL APPLICABILITY

The present invention is applicable to a cell culture method that cultures cells isolated from tissue.

The invention claimed is:

1. A cell culture method comprising:
   culturing fetal liver cells in a layered state in a partitioned micro-space, thereby obtaining a cell mass containing differentiated liver parenchymal cells,
   wherein
   the fetal liver cells differentiates in the partitioned micro-space, and
   the fetal liver cells are at least one of fetal liver stem cells and fetal liver precursor cells.

2. The method of claim 1, wherein the fetal liver cells are human cells.

3. The method of claim 1, wherein the partitioned micro-space is a space in a micro-container having the micro-container on a surface.

4. The method of claim 3, wherein the micro-container has a bottom having no through hole.

5. The method of claim 3, wherein the micro-container has a bottom surface area of $9 \times 10^{-4}$ mm$^2$ to $9 \times 10^{-2}$ mm$^2$.

6. The method of claim 3, wherein the micro-container has a side wall with a height of 15 μm to 300 μm.

7. The method of claim 3, wherein a side wall has a height of 15 μm to 150 μm.

8. The method of claim 3, wherein a side wall has a height of 50 μm to 150 μm.

9. The method of claim 3, wherein the cell culture container having a plurality of the micro-containers on the surface.

10. The method of claim 9, wherein a side wall has a width of 3 μm to 15 μm.

11. The method of claim 9, wherein the micro-container has the width b and the height c of a side-wall satisfying the following relations:
   3 μm≤b ≤15 μm and c/b ≥2.

12. The method of claim 9, the cell culture container includes a plurality of partitioned spots each made up of the plurality of micro-containers.

13. The method of claim 3, wherein a region where the micro-container is formed in the cell culture container has transparency.

14. The method of claim 3, wherein a culture seeding density in the micro-container is from $1.0 \times 10^4$ to $5.0 \times 10^6$ cells/cm$^2$.

15. The cell culture method according to claim 3, wherein the micro-container has a rectangular shape of the bottom surface and a longer side of the micro-container is from 1 to 1.5 times longer than a shorter side.

* * * * *